United States Patent [19]
Hausmann et al.

[11] Patent Number: 5,629,972
[45] Date of Patent: *May 13, 1997

[54] INTRAORAL RADIOGRAPH ALIGNMENT DEVICE

[75] Inventors: Ernest Hausmann, Amherst; Darold Wobschall, Williamsville; Lance Ortman, Snyder, all of N.Y.; Evren Kutlubay, San Jose, Calif.; Kristin Allen, Buffalo; David Odrobina, West Seneca, both of N.Y.

[73] Assignee: Research Foundation of State University of New York, Buffalo, N.Y.

[*] Notice: The term of this patent shall not extend beyond the expiration date of Pat. No. 5,513,240.

[21] Appl. No.: 552,591

[22] Filed: Nov. 3, 1995

Related U.S. Application Data

[63] Continuation-in-part of Ser. No. 63,590, May 18, 1993, Pat. No. 5,513,240.

[51] Int. Cl.$^6$ .................................................... A61B 6/14
[52] U.S. Cl. ........................... 378/170; 378/168; 378/205
[58] Field of Search ................................. 378/167, 168, 378/169, 170, 177, 205

[56] References Cited

U.S. PATENT DOCUMENTS

| | | | |
|---|---|---|---|
| 3,745,344 | 7/1973 | Updegrave | 250/70 |
| 4,012,638 | 3/1977 | Altschuler et al. | 250/491 |
| 4,223,228 | 9/1980 | Kaplan | 250/491 |
| 4,554,676 | 11/1985 | Maldonado et al. | 378/170 |
| 4,949,370 | 8/1990 | Tanaka | 378/170 |
| 5,090,047 | 2/1992 | Angotti et al. | 378/170 |
| 5,513,240 | 4/1996 | Hausmann et al. | 378/170 |

OTHER PUBLICATIONS

Guillemin et al., "Healing in periodontal defects treated by decalcified freeze-dried bone allografts in combination with e PTFE membranes", Journal of clinical periodontology, 1993, pp. 520–527 no month.

*Primary Examiner*—David P. Porta
*Attorney, Agent, or Firm*—Heslin & Rothenberg, P.C.

[57] ABSTRACT

The invention is an apparatus for use in serial radiography which provides replicable projection geometry between an energy source, an intraoral target area, and an image receptor. The device uses a biting surface bearing the impressions of a patient's tooth surfaces and an alignment arm which terminates in an alignment ring. The alignment ring is received by a sensor ring affixed to an x-ray source to provide proper projection geometry. Sensors in communication with electronic means may be disposed about the sensor ring to indicate proper alignment. The biting surface may comprise an acrylic stent or a platform supporting a quantity of an impressionable material.

16 Claims, 10 Drawing Sheets

Fig_ 6

Fig_7

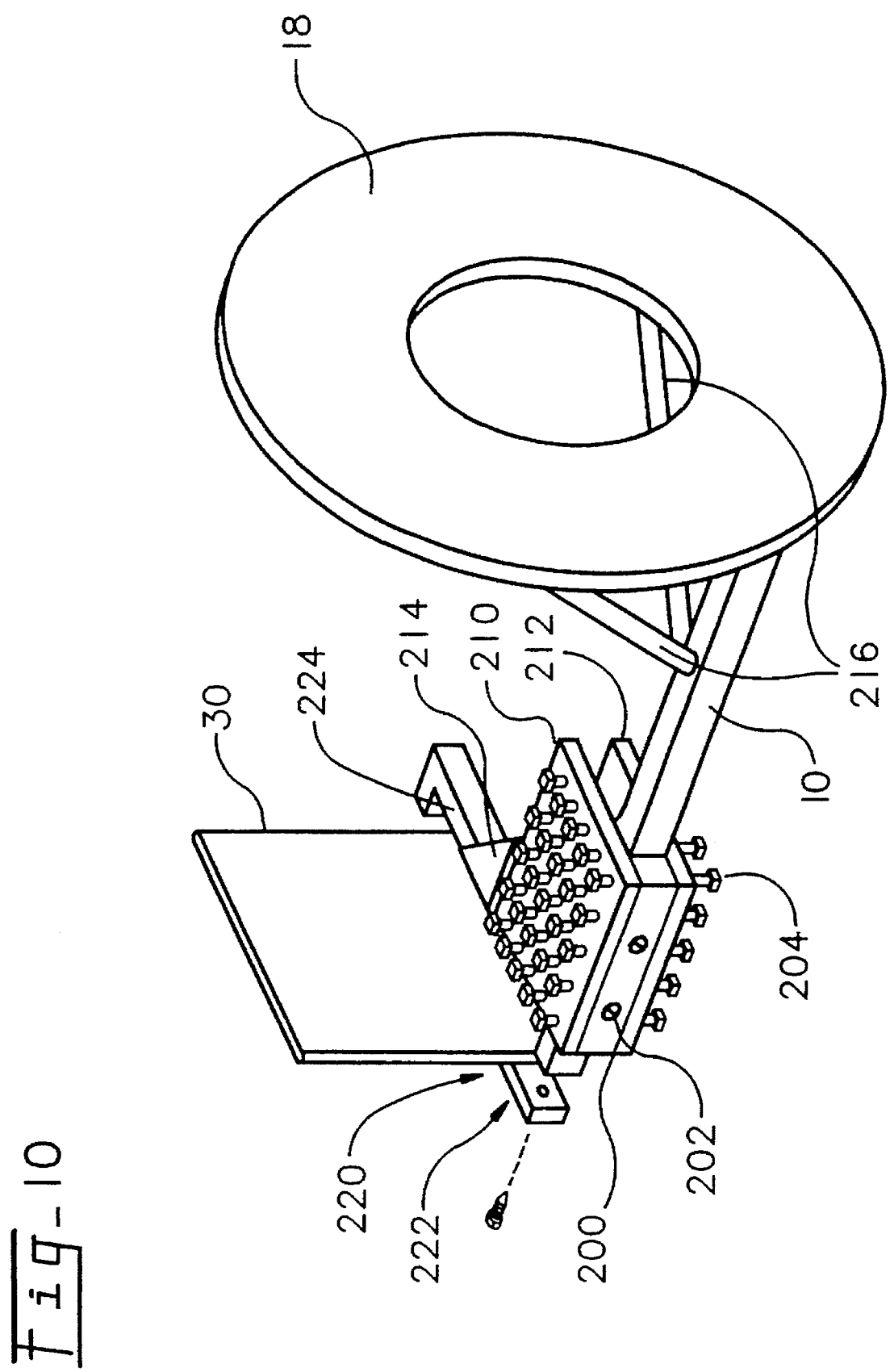

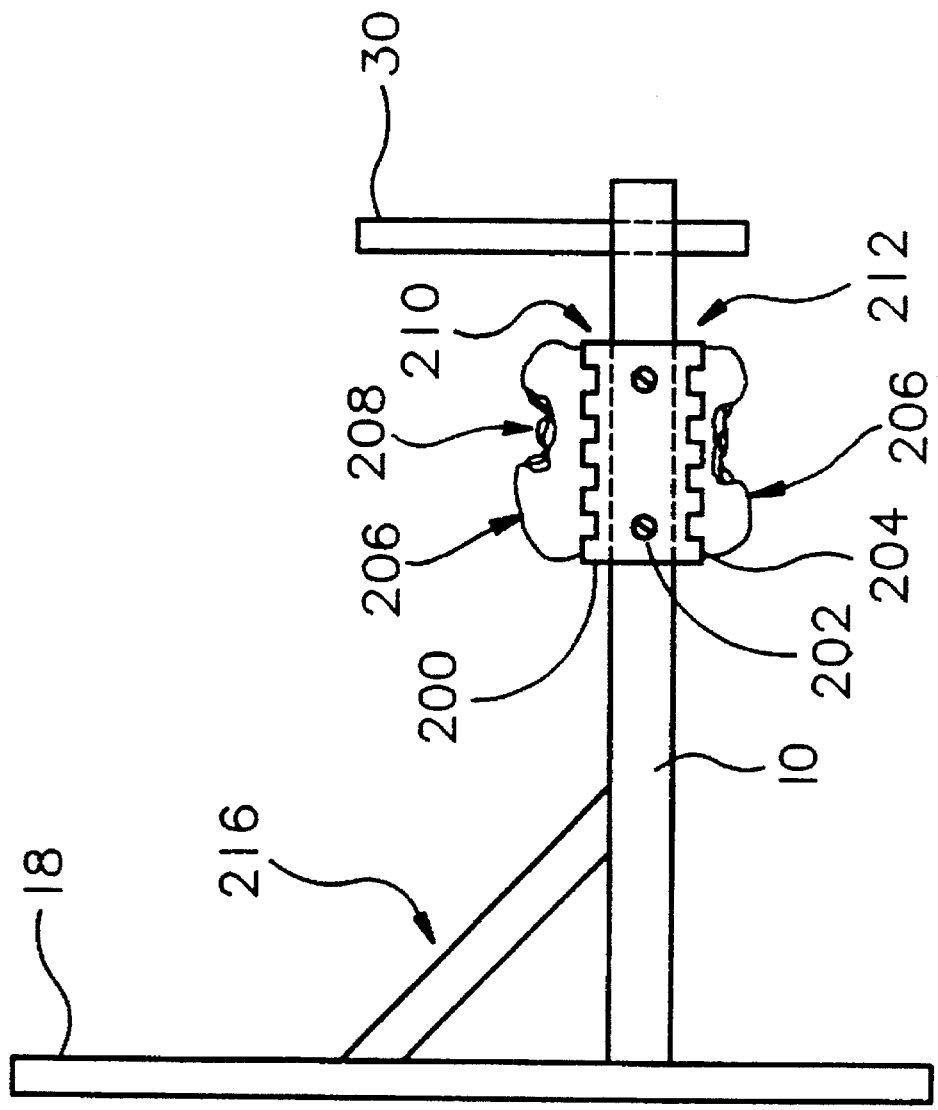

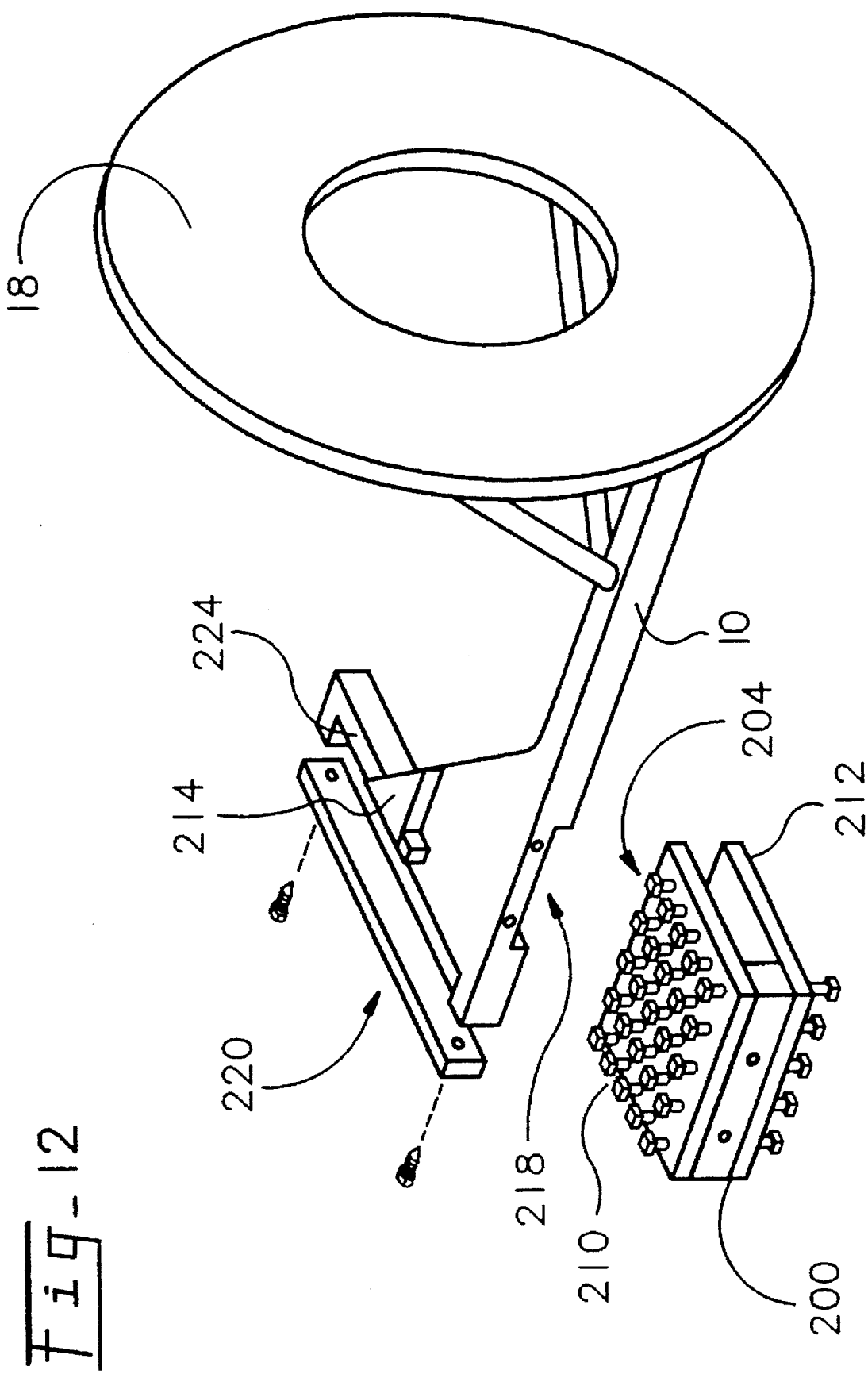
Fig_12

INTRAORAL RADIOGRAPH ALIGNMENT DEVICE

This application is a continuation in part of Ser. No. 08/063,590, filed May 18, 1993, now U.S. Pat. No. 5,513,240.

BACKGROUND OF THE INVENTION

The present invention is an apparatus for use in serial radiography which provides replicable projection geometry between an energy source, an intraoral target area, and an image receptor.

The use of the radiograph as a tool for observation and diagnosis has played a significant role in the development of dental medicine. A single radiograph can reveal a multitude of information which is not available to the naked eye. One particularly useful application of the radiograph is serial radiography, in which two radiographs of a target area are compared to reveal changes occurring in that area during the time elapsed between exposures. Serial radiography is employed, for example, to recognize the loss of alveolar bone tissue which can result from periodontal disease. The technique is enhanced by digital subtraction, which uses computer analysis of digitized radiographs to locate areas of change between successive images.

To properly perform serial radiography, it is essential that the projection geometry of successive images be as near to identical as possible, since the discrepancies between two images with dissimilar projection geometry may mask areas in which tissue has been lost, or, conversely, may indicate loss of tissue where none has actually occurred. Within the prior art, one method has been developed to correct imaging errors resulting from misalignment of the x-ray source and image receptor between images which have no misalignment of the x-ray source and target area. However, no method has yet been developed to correct imaging errors resulting from misalignment of the x-ray source and the target area. As a result, the effectiveness of serial radiography for diagnosis of tissue loss is wholly dependent upon the ability of the radiographer to provide precise replication of projection geometry for every exposure.

In dental radiography, several types of devices for achieving satisfactory alignment of energy source, target area, and image receptor have been employed. One is the cephalostat, a device which by means of ear rods fixes a patient's head in a desired position bearing a fixed or otherwise known spatial relationship to an x-ray source. Stent based devices, in contrast, use a biting surface which is held between the teeth, and which provides alignment through some means extending from the biting surface toward the x-ray source. However, most devices of this type were developed before the advent of serial radiography, and therefore were not designed to provide alignment within the requisite tolerances. Several of these merit individual description.

Updegrave, U.S. Pat. No. 3,745,344, INTRAORAL SYSTEM FOR SUBSTANTIALLY CONFINING THE X-RAY BEAM TO THE FILM, Jul. 10, 1973, teaches a rectangular collimating tube which is affixed to and extends from an x-ray source toward a target area. A guide rod extending from the end of the collimating tube terminates in a bite plate which supports a film holder and which is held between the patient's teeth.

Maldonado, U.S. Pat. No. 4,554,676, DENTAL AIMING DEVICE, Nov. 19, 1985, teaches an aiming device comprising an alignment arm which terminates at one end in a bite plate supporting a film holder. The other end of the arm is fitted with an alignment ring to be positioned against the collimating tube of an x-ray source, thereby roughly achieving alignment between source, target, and film.

Angotti, U.S. Pat. No. 5,090,047, APPARATUS FOR POSITIONING AN IMAGE RECEPTOR FOR INTRAORAL DIAGNOSTICS, Feb. 18, 1992, teaches an aligning arm which is fixed at one end to the collimating tube of an x-ray source, and which terminates at the other end in a bite block and a film holder.

Altschuler, U.S. Pat. No. 4,012,638, DENTAL X-RAY ALIGNMENT SYSTEM, Mar. 15, 1977, teaches a reflective ring mounted to a flexible arm and film holder. The reflective ring is directed toward an infrared sensor/emitter array which detects ring alignment.

Kaplan, U.S. Pat. No. 4,223,228, DENTAL X-RAY ALIGNING SYSTEM, Sep. 16, 1980, teaches a Hall effect sensor array mounted about an x-ray apparatus for detecting alignment of a film package carrying a magnet.

The prior art devices to date do not provide the optimal means for achieving replicable projection geometry. Devices such as Updegrave, which require visual alignment of two unconnected objects, do not restrict the patient's movement to within a range likely to reproduce a prior alignment, and do not supply a reliable reference surface for alignment. Conversely, devices such as Maldonado and Angotti rely solely on the mechanical integrity of a fixed system. A deformation or other alteration of the fixed alignment of the system with respect to the x-ray source, whether resulting from the movement of a patient or any other incident force, may render useless for purposes of comparison those radiographs taken before the alteration occurred. Additionally, the fixed nature of such devices may make them awkward for the patient to use.

SUMMARY OF THE INVENTION

The present invention provides a system which overcomes the limitations inherent in the prior art. The system comprises a rigid alignment arm which is perpendicular to and extends from an alignment ring, and which at its other end supports a biting surface and an image receptor in a fixed relationship to the alignment ring. The system further comprises a sensor ring having a planar face which is fixed about the collimating tube such that the planar face is perpendicular to the x-ray beam. The alignment ring is received by the sensor ring between a plurality of alignment pins such that the alignment ring, sensor ring, and collimating tube are concentric. Due to the fixed relationship among the elements of the alignment arm, and the flat surfaces of the alignment ring and sensor ring, a replicable alignment is achieved when the face of the alignment ring is pressed flatly against the face of the sensor ring. The sensor ring may further have disposed about its face an array of sensors in communication with electronic means, for detecting when flat contact between the sensor ring and alignment ring has occurred. When force exceeding a predetermined minimum threshold is detected at each sensor contemporaneously, flat contact between rings has occurred, and a display means indicates that proper alignment of the elements has been achieved. By permanently affixing the sensor ring to the x-ray source, the system can be used to replicate projection geometry within the tolerances necessary for serial radiography.

In operation, a bite block or stent is formed for each individual patient from acrylic or some other impressionable substance. The bite block may bear the impression of the surfaces of the maxillary or the mandibular teeth, or both. A stent insert is incorporated into the stent material. The stent insert has three apertures, one of which is threaded, to facilitate mounting of the stent to the alignment arm. The stent insert is positioned within the stent such that, when attached to the alignment arm, the stent will assume a desired orientation with respect to the arm and an image receptor, and thereby, when in use, to the x-ray beam.

The alignment arm is composed of steel or some other sufficiently rigid material. Rigidity must be such that an incident force of one pound at the stent end of the arm will cause a deflection of no more than one degree. This limit was chosen because serial radiography requires that the sum of all angular deviations between serial images be less than one degree, and because a force of greater than one pound will cause displacement of the x-ray source itself.

At one end the alignment arm supports a film holder or other image receptor, the planar surface of which is perpendicular to the arm. Near the image receptor the alignment arm supports a biting surface which may be repeatedly mounted to the arm in an exact desired orientation.

Near its midpoint, the alignment arm may be provided with a series of ninety degree angles which together form an offset in the path of the arm. This offset is useful for exposures of the posterior teeth, wherein the patient's cheek prevents the use of an arm leading straight from the stent toward the x-ray source. At its opposite end, the alignment arm branches to form a triangle, the base of which is affixed by screws or other means to the face of a plate-like alignment ring composed of the same material, such that the plane of the alignment ring is perpendicular to the alignment arm. In operation, the biting surface is held in position between the patient's teeth, and the alignment arm and ring extend toward the x-ray source. The arm is preferably as short as possible, to reduce the amount of x-ray energy necessary for sufficient exposure, to minimize the potential for flexion under normally encountered loads, and to minimize weight.

Affixed at the end of the collimating tube of the x-ray source, and concentric with the tube, is the sensor ring. The ring is held in place by a screw threaded through the ring and terminating at the inner surface of the sensor ring in frictional contact with the outer surface of the collimating tube. Extending from the flat circular face of the sensor ring are a plurality of cylindrical alignment pins which receive the alignment ring between them.

About the face of the sensor ring are disposed several force sensors. Since replicable alignment is achieved by placing the alignment ring flatly in contact with the sensor ring, alignment is indicated when sufficient force beyond a minimum threshold is caused by the alignment ring contemporaneously at each sensor. In practice it has been found that alignment ring contact forces of one ounce at each sensor reliably indicate that the alignment ring is flatly in contact with the sensor ring, and therefore that alignment replicable within the requisite tolerances has been achieved. In practice, any two radiographs which are made using the same alignment arm and stent and which are taken when proper alignment is indicated will have projection geometries which are sufficiently alike to allow their use for serial radiography. It has been empirically determined that the contribution of the sensors to the deflection of the total system is less than 0.1 degree.

To facilitate use of the device by the patient, a display is provided which is visible to the patient during operation to indicate the direction in which the patient's head orientation must shift to achieve acceptable alignment, as well as to indicate when acceptable alignment has been achieved. It is contemplated that in future embodiments the electrical signal which indicates acceptable alignment may also be used to enable or trigger the x-ray source, as well as to enable an electromagnetic latching of the alignment ring to the sensor ring. A goose-neck may be used to support the display within the field of view of the patient. To facilitate and maintain contact between the alignment ring and sensor ring, several weak magnets may be disposed about the face of the sensor ring. A handle may also be provided on the collimating tube of the x-ray source to aid the patient in maintaining the position of the alignment ring with respect to the sensor ring.

BRIEF DESCRIPTION OF THE DRAWINGS

FIG. 10 illustrates an improved embodiment of the invention featuring a platform for supporting a quantity of an impression material.

FIG. 11 illustrates the embodiment of FIG. 10 supporting a quantity of an impression material.

FIG. 12 provides an exploded view of the embodiment of FIG. 10.

DETAILED DESCRIPTION OF A PREFERRED EMBODIMENT

Figure 1:
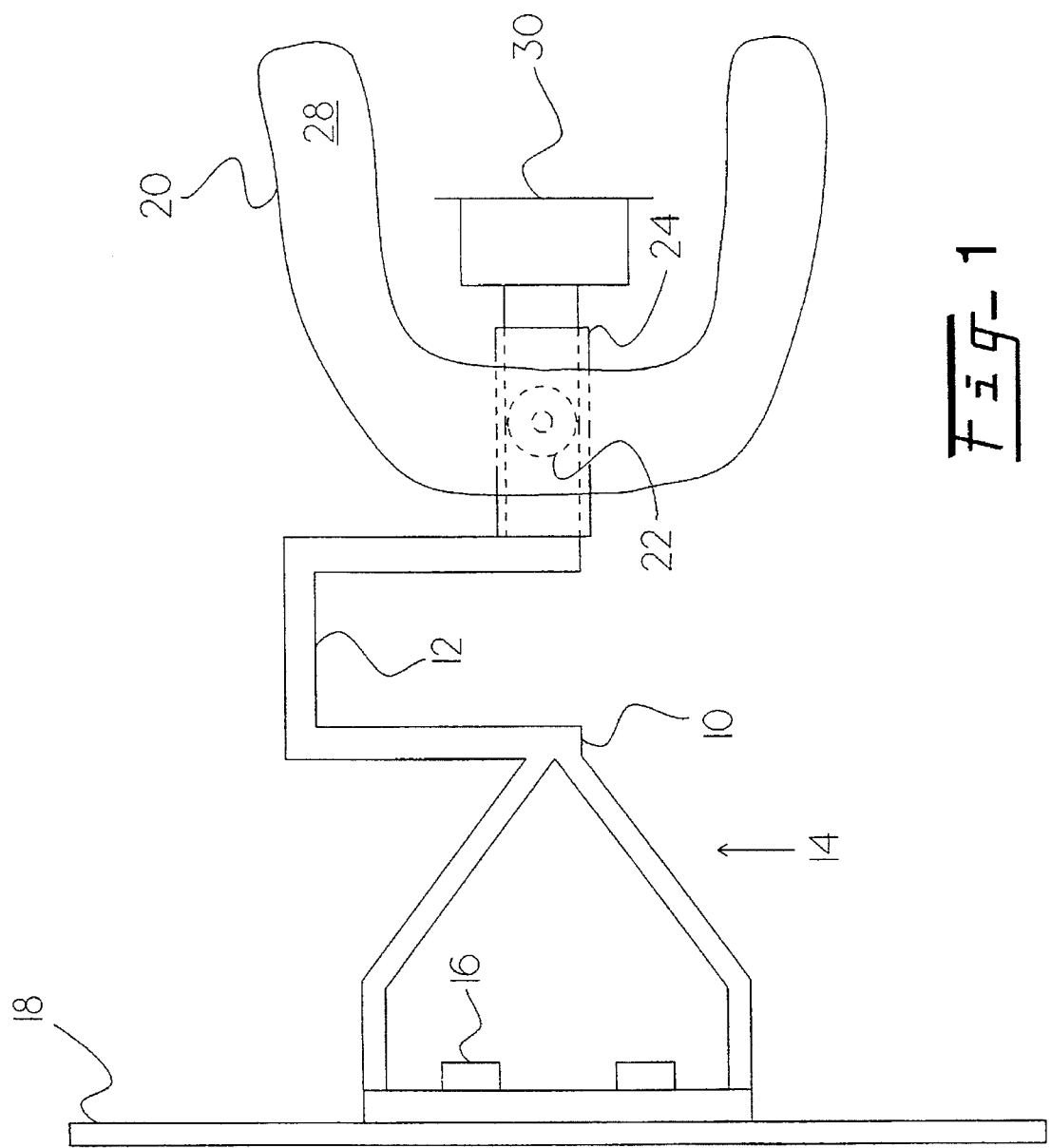
FIG. 1 shows a view from above of the alignment arm and ring, including a stent affixed to the arm.
Figure 2:
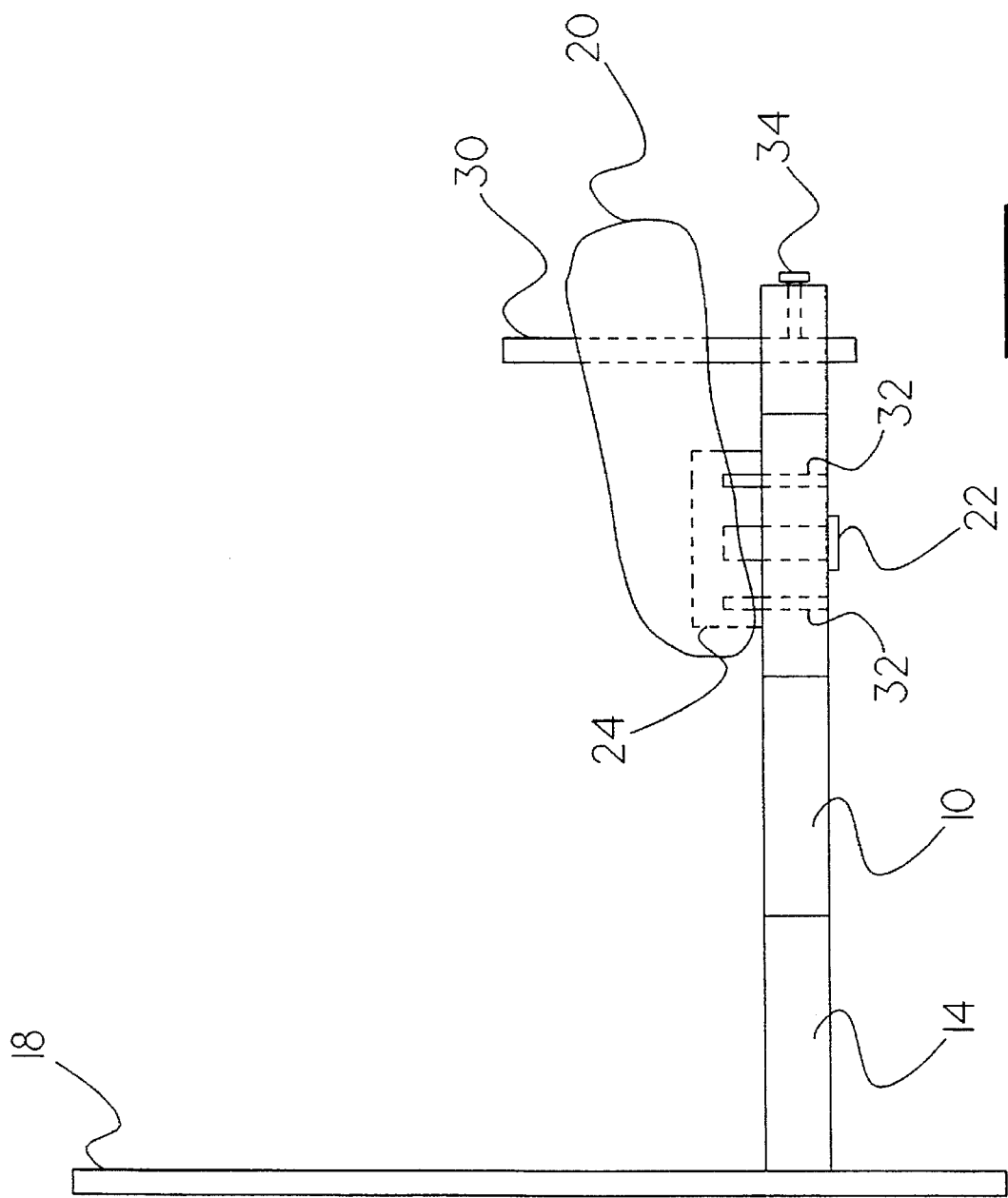
FIG. 2 shows a side view of the device of FIG. 1.
Figure 3:
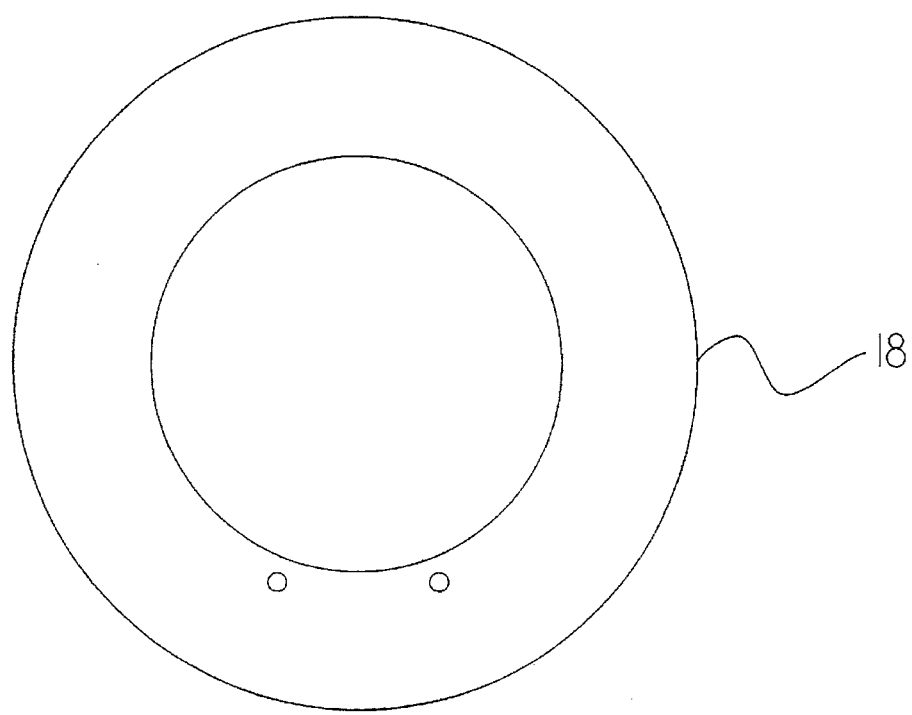
FIG. 3 shows the face of the alignment ring which makes contact with the sensor array.
Figure 6:
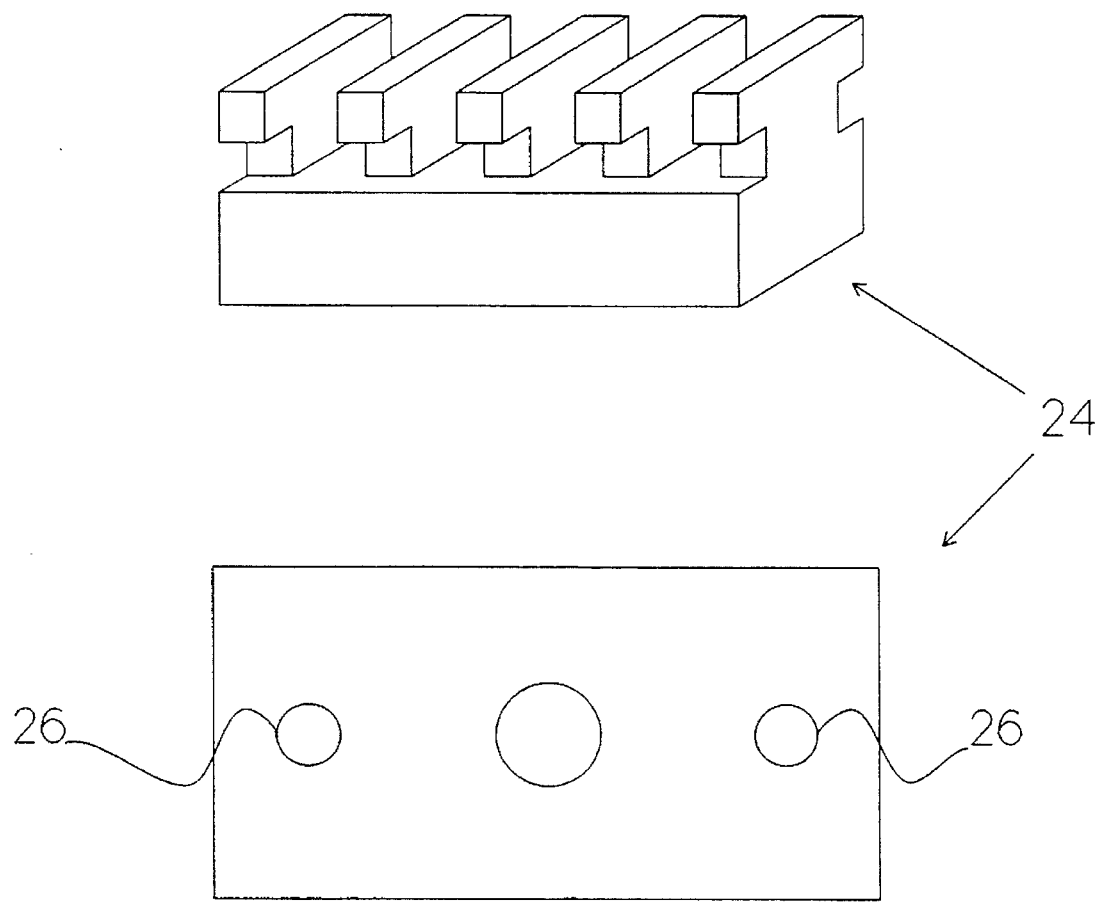
FIG. 6 provides an elevated view and a bottom view of the stent insert.

Referring now to the drawings, there is shown in FIG. 1 an alignment arm 10 including a cheek offset 12 and a branched end section 14. The offset as shown is useful for both frontal exposures and exposures from the upper left side and lower right side of the face. For exposures from the upper right side and lower left side of the face, an alignment arm having an offset of opposite orientation with respect to the bite block would be used. Affixed with screws 16 to the branched end section is the alignment ring 18, a frontal view of which is provided in FIG. 3. At the opposite end of the aligning arm, an acrylic bite block 20 is affixed with a screw 22 which passes from the lower side of the alignment arm 10 into a stent insert 24 having a series of slots and grooves for firm retention within the material of the bite block, as is illustrated in FIG. 6. Two alignment pins 32 as shown in FIG. 2 are also received into cylindrical apertures 26 in the stent insert. The bite block bears the impression of a patient's tooth surfaces on its upper surface 28. Disposed within the circumference of the bite block 20 is a film holder 30 for holding a film packet in alignment with respect to the bite block, and thereby with respect to the intended target area.

FIG. 2 provides a side view of the apparatus as shown in FIG. 1. From this perspective the bite block screw 22 and alignment pins 32 can be seen extending through the alignment arm 10 and into the stent insert 24. FIG. 2 also illustrates the film holder screw 34 which allows for adjustment of the height of the film packet held therein with respect to the bite block.

Figure 4:
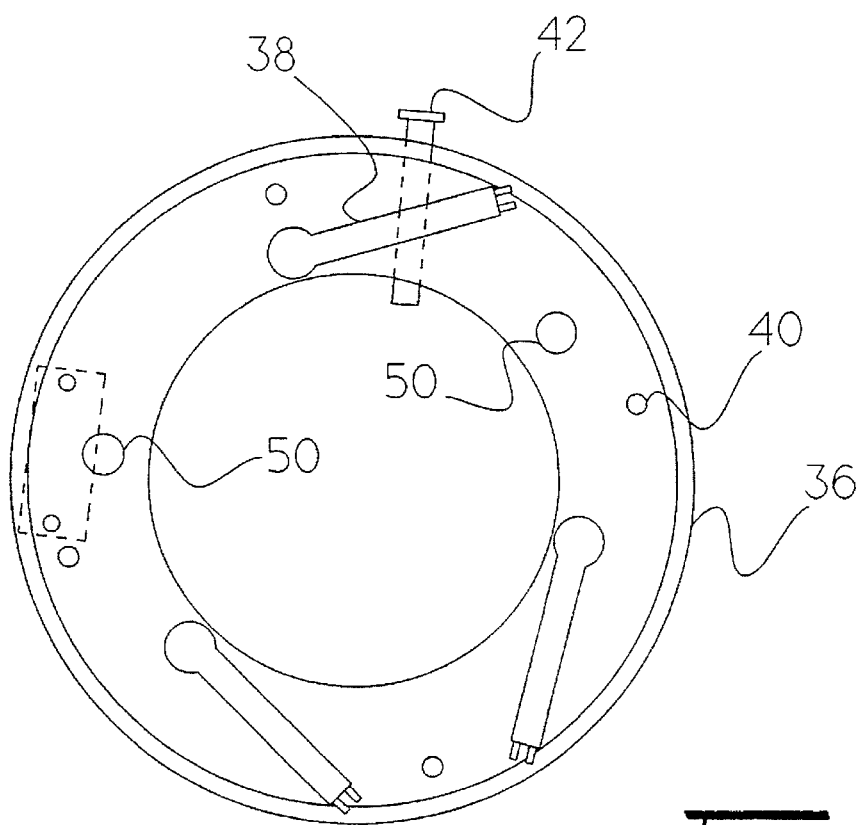
FIG. 4 shows the face of the sensor ring including three force sensors and four alignment pins.
Figure 5:
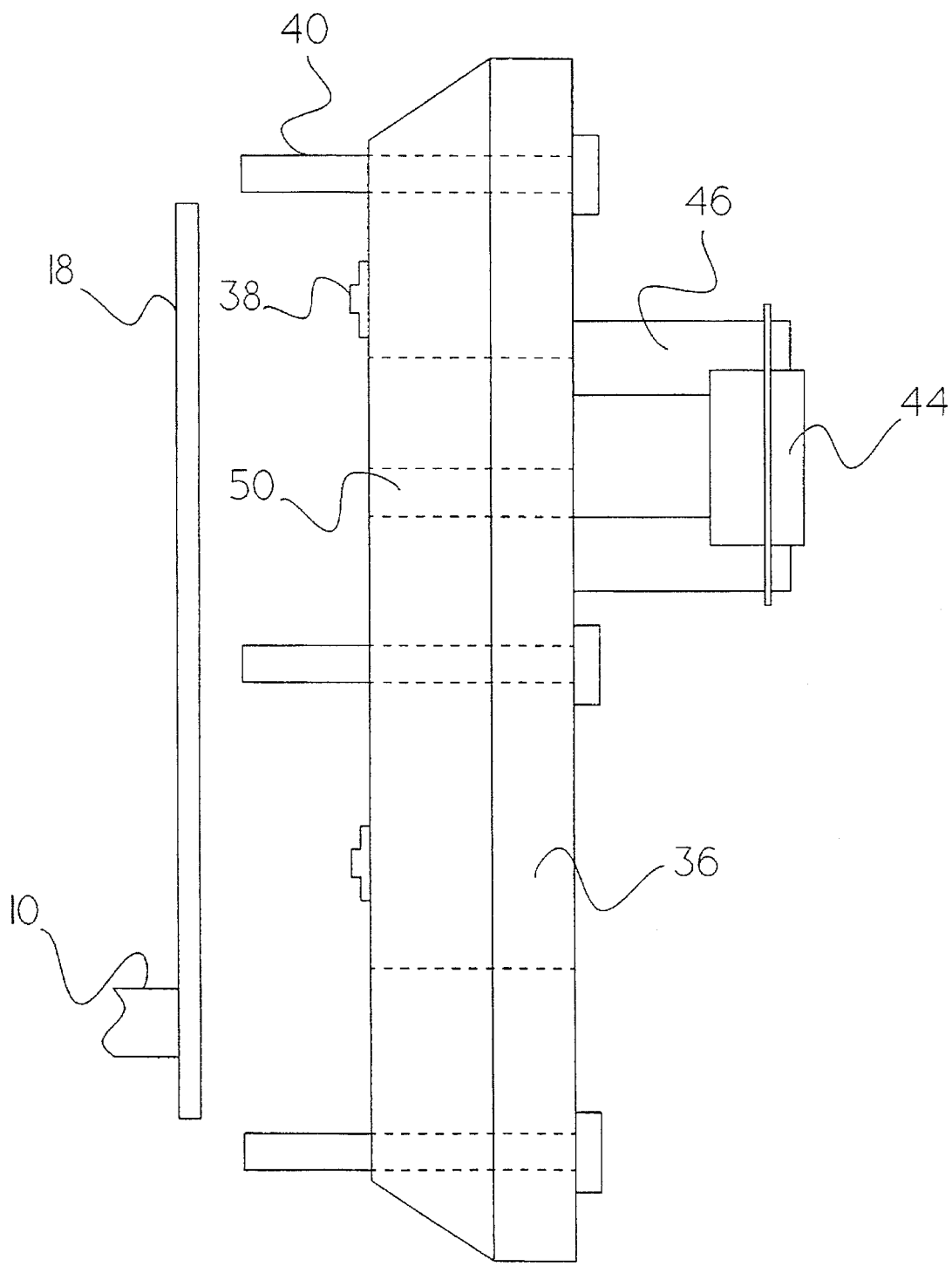
FIG. 5 shows a side view of the alignment ring being received by the sensor ring.

FIG. 4 shows the face of the sensor ring 36. Disposed about the face of the plexiglass ring in a triangular orientation are three resistive force sensors 38. At least three such sensors are necessary to provide a plane for contact with the alignment ring. While more than three sensors may be used, this tends to introduces an unnecessary level of complexity into the device. Further provided on the face of the sensor ring are weak magnets 50 which aid the patient in placing the alignment ring in contact with the sensor ring. Disposed about the outer edge of the face of the sensor ring are four alignment pins 40. These pins are placed such that the largest possible radius of a circle inscribed between them is slightly larger than the outer radius of the alignment ring. The alignment ring 18 is illustrated in relation to the alignment pins 40 in FIG. 5. The sensor ring 36 is held in place about the cylindrical collimator of an x-ray source (not shown) by tightening a screw 42 which passes through the sensor ring to terminate in frictional contact against the collimator.

Figure 8:
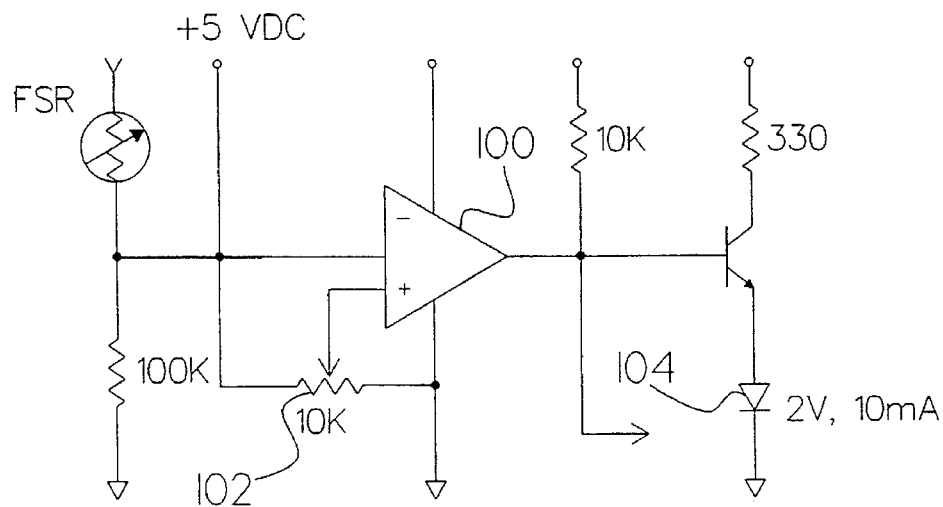
FIG. 8 illustrates a comparator circuit including a force sensor and a display LED.

Wires from the sensors 38 are routed to a nine-pin connector 44 situated on a mount 46. A cable (not shown) is used to connect each sensor to a comparator circuit as illustrated in FIG. 8. Each comparator consists of an op-amp 100 which receives at its positive terminal input from a sensor 38, and at its negative terminal a threshold voltage determined by the value of a variable threshold resistor 102. As force is increased on the force sensor, its resistance drops, thereby increasing the voltage to the positive terminal such that at the threshold point the output of the op-amp 100 will swing positive and light a corresponding red display LED 104. It has been found that thresholds of one ounce at each sensor are sufficient to indicate proper alignment.

Figure 9:
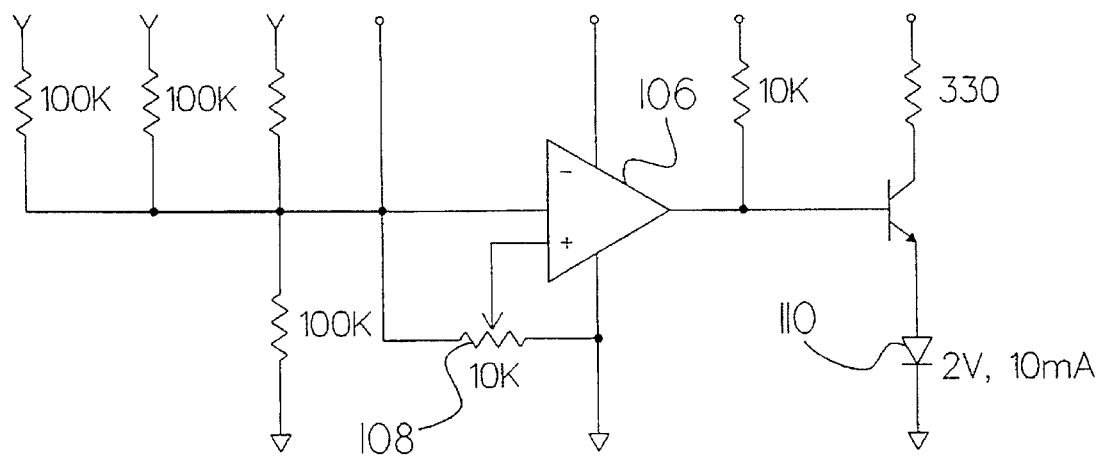
FIG. 9 illustrates a second comparator circuit receiving input from the comparators of each force sensor and including a display LED.

The outputs from each sensor/comparator circuit are also fed to a second op-amp comparator 106, illustrated in FIG. 9, which compares the sum of the sensor circuit output voltages to a second threshold determined by a second threshold resistor 108. This threshold is set such that all three sensor circuits must be indicating proper alignment to swing the second comparator circuit positive. When this occurs, power is provided to light an additional red display LED 110, which indicates to the user that acceptable projection geometry has been achieved. The output signal from this comparator may also be used in conjunction with other electronic means to enable or trigger the x-ray source, or to enable an electromagnetic latch.

Figure 7:
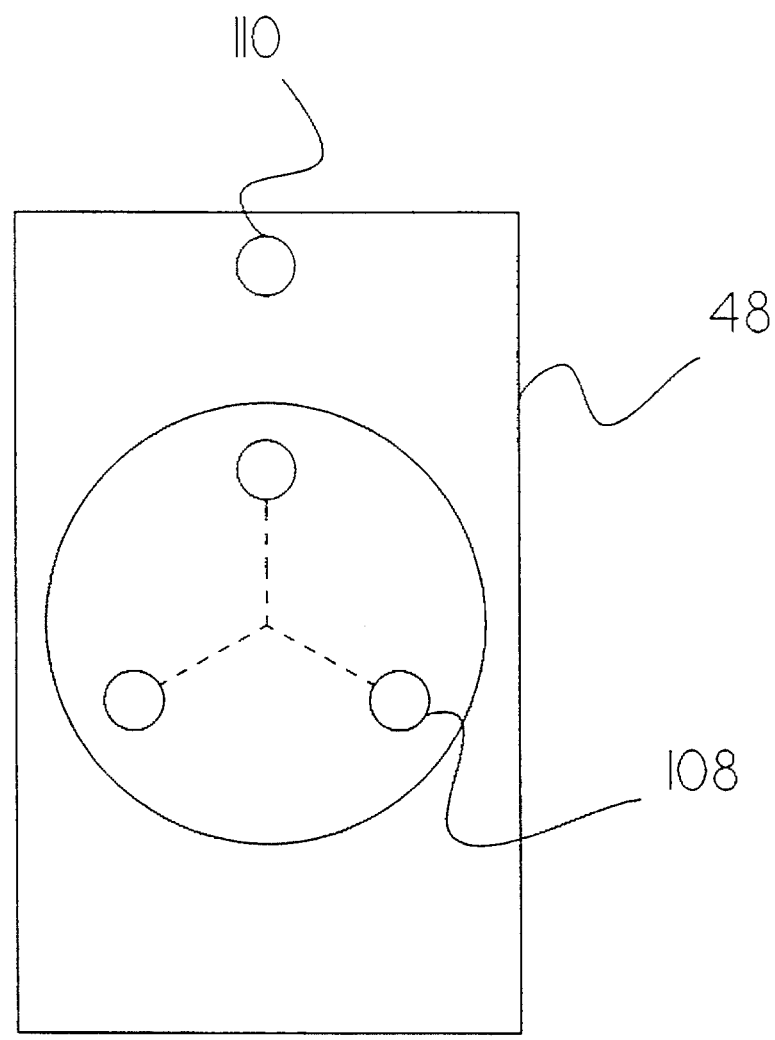
FIG. 7 is a front view of the display module including three LED's for indicating proper force at each sensor, and a fourth LED for indicating proper overall alignment.

The display LED's are disposed in a housing 48, illustrated in FIG. 7, and are oriented in a manner which corresponds to the positions of their respective sensors relative to the face of the sensor ring. Prior to operation, the sensor array is made visible to the patient, and during operation an LED is lit when sufficient force is detected at its corresponding sensor. In this manner it is indicated to the patient the direction in which his head orientation must be shifted to achieve proper alignment.

IMPROVED EMBODIMENT

In an improved embodiment, the stent may be replaced with a platform supporting a quantity of an impression material which has been provided with impressions of the patient's tooth surfaces. FIGS. 10 through 12 illustrate an exemplary embodiment.

Referring first to FIG. 10, the arm 10 of the improved embodiment supports a platform 200 which is mounted to the arm in a fixed relationship to the image receptor 30. The platform is made of a relatively inflexible material such as hard plastic. The platform 200 of the illustrated embodiment can be seen to comprise complementary faces 210 and 212. As illustrated in FIG. 11, the platform 200 is used to support a quantity 206 of an impression material on one or both of its surfaces. The impression material is prepared so as to bear impressions 208 of a patient's tooth surfaces. In this manner the material serves to facilitate replicable alignment of the arm 10 and image receptor 30 with the patient's teeth.

The surface of the platform faces 210 and 212 may be provided with a texture to facilitate adhesion of the impression material. FIGS. 10 through 12 show a platform faces having regular arrays of raised portions 204 protruding from their surfaces. The raised portions should be of sufficient height to protrude into the impression material a sufficient distance to retain the impression material against the shearing and tensile forces which will be encountered during use.

The platform is preferably removable. As illustrated in FIG. 12, the platform may be comprised of a single unit which is removably mountable to the arm 10. A slot 218 provided in the arm 10 serves to align the platform 210 in a predetermined fixed relationship to the arm 10. The platform may be held in place by screws 202 or some other appropriate means to retain its position during use.

The impression material used with the platform described above must be capable of retaining tooth surface impressions between instances of use and must be sufficiently rigid to resist significant deformation once impressions have been made. Preferred for this application is polyvinyl siloxane, a material which is well-known in the field for taking impressions of teeth. Those skilled in the art will be aware of the general manner of preparation and use of polyvinyl siloxane. To prepare an impression for use with the present invention, a quantity of material in its impressionable state is affixed to one or both surfaces of the platform. The platform is mounted to the arm in a position which is appropriate to produce the desired images, and the impression material is bitten upon by the patient. After a hardening time of approximately five minutes, during which the material should remain under compression between the patient's teeth, the material becomes sufficiently rigid to retain tooth surface impressions. The platform with its impression material may then be used in the manner described above. Impressions made from polyvinyl siloxane are known to be storable and reusable for months or years.

It has been found that the best mode presently known for practicing the invention includes the use of a triangular calibration wedge placed near the image receptor with its plane orthogonal to the plane of the image receptor. Such devices are well known in the field. Typically the wedge is formed of aluminum, which has roughly the same density as teeth. The wedge produces an image having an intensity which is graduated with the thickness of the triangle. This image provides a reference which assists in the estimation of the tissue thickness and loss represented in an image. A triangular calibration wedge 214 may be seen in FIGS. 10 and 12.

It has further been found that the best mode of practicing the invention includes the use of an arm 10 which extends along a line relative to the patient such that a cheek offset is not required. FIG. 10 shows an example of such an arm 10. The arm is supported by two supporting arms 216 which connect the arm 10 to the alignment ring 18.

In addition, it is preferable to use an image receptor mounting means as illustrated in FIGS. 10 and 12, in which a bar 220 provided with screw holes 222 is used to clamp an image receptor 30 to a back portion 224 of the arm at right angles to the arm 10. The image receptor is preferably provided with a plastic backing (not shown).

While this apparatus and various methods of its use have been shown completely in terms of particular embodiments and applications, one of ordinary skill in the art may generate additional embodiments and applications which do not depart from the spirit or exceed the scope of the claimed invention, and it should therefore be understood that within the scope of the claims the invention may be practiced otherwise than as specifically described.

What is claimed is:

1. An apparatus for providing a replicable projection geometry between an energy source, an intraoral target area, and an image receptor, comprising:

a rigid alignment arm, supporting at one end an alignment ring, and supporting at its opposite end an image receptor, the plane of said alignment ring being perpendicular to said alignment arm and said alignment ring having a planar face;

a platform mountable to said arm a fixed relationship to said image receptor, said platform supporting a quantity of a material bearing impressions of a patient's tooth surfaces; and, a sensor ring, mountable about an energy beam source and having a planar surface for engaging the planar face of said alignment ring, whereby flat contact between the planar surfaces of said alignment ring and sensor ring produces a replicable projection geometry between said energy beam source, target area, and image receptor.

2. The apparatus of claim 1, wherein said impressionable material is polyvinyl siloxane.

3. The apparatus of claim 1, further comprising:

a plurality of sensors disposed about the planar surface of said alignment ring, for sensing contact with said alignment ring; and, electronic means in communication with said sensors, for determining from the output of said sensors the attainment of an acceptable projection geometry.

4. The apparatus of claim 3, wherein said sensors are resistive force sensors.

5. The apparatus of claim 3, wherein said electronic means include comparators in communication with each of said sensors.

6. The apparatus of claim 3, further comprising:

display means in communication with said electronic means, for indicating to a user the attainment of an acceptable projection geometry.

7. The apparatus of claim 6, wherein said display means comprises a plurality of LEDs, each of said LEDs corresponding to one of said plurality of sensors, said LEDs being oriented in a manner corresponding to the relative position of their respective force sensors on said sensor ring, each of said LEDs being lit when sufficient force is detected by said LED's respective sensor.

8. The apparatus of claim 7, further comprising an LED for indicating the achievement of acceptable alignment.

9. The apparatus of claim 1, further comprising at least one magnet on the face of said sensor ring for facilitating contact between said alignment ring and said sensor ring.

10. The apparatus of claim 1, wherein said image receptor is adjustable in height with respect to said biting surface.

11. The apparatus of claim 1, wherein said alignment arm includes an offset adjacent to said bite block for circumventing a patient's cheek.

12. The apparatus of claim 1, wherein said image receptor comprises a film packet.

13. The apparatus of claim 1, further comprising a triangular calibration wedge affixed to said arm and having its plane aligned orthogonally to the plane of said image receptor.

14. A method for producing a radiograph, comprising:

(a) providing a first structure having a surface oriented in a fixed relationship to an energy beam of an energy beam source, said surface facing generally in the direction of emission of said energy beam;

(b) providing a second structure bearing a surface complementary to said surface of said first structure, said second structure further bearing an image receptor and a biting surface oriented in a fixed relationship to said surface of said second structure, said biting surface bearing impressions of a patient's tooth surfaces, said biting surface being disposed between said complementary surface and said image receptor, said biting surface and said image receptor being oriented generally along a line orthogonal to said complementary surface;

(c) placing said biting surface between the teeth of a patient from whose teeth said impressions were formed, such that said teeth are situated within said impressions;

(d) placing into contact said surface of said first structure and said complementary surface of said second structure; and (e) exposing said image receptor to an energy beam emitted by said energy beam source.

15. The method of claim 14, wherein said biting surface comprises a stent.

16. The method of claim 14, wherein said biting surface comprises a platform supporting a quantity of material bearing impressions of said patient's tooth surfaces.

* * * * *